United States Patent [19]

Pews et al.

[11] Patent Number: 5,089,653

[45] Date of Patent: Feb. 18, 1992

[54] PROCESS FOR THE SELECTIVE REDUCTION OF THE 4-HALOGEN IN 2,4-DIHALOANILINES

[75] Inventors: R. Garth Pews, Midland, Mich.; Richard M. Wehmeyer, Lake Jackson, Tex.; James E. Hunter, Walnut Creek, Calif.

[73] Assignee: Dow Elanco, Indianapolis, Ind.

[21] Appl. No.: 680,712

[22] Filed: Apr. 4, 1991

[51] Int. Cl.⁵ .............................. C07C 229/00
[52] U.S. Cl. ...................... 560/47; 562/456; 564/412
[58] Field of Search .............. 560/47; 562/456; 564/412

[56] References Cited

U.S. PATENT DOCUMENTS

| | | | |
|---|---|---|---|
| 4,070,401 | 1/1978 | Hirai et al. | 562/456 |
| 4,085,141 | 4/1978 | Wedemeyer et al. | 564/412 |
| 4,193,937 | 3/1980 | Wedemeyer et al. | 564/412 |
| 4,206,147 | 6/1980 | Daunas et al. | 564/412 |
| 4,206,148 | 6/1980 | Biola et al. | 564/412 |
| 4,418,213 | 11/1983 | Cordier et al. | 564/412 |
| 4,429,156 | 1/1984 | Wedemeyer et al. | 564/412 |
| 4,460,788 | 7/1984 | Wedemeyer et al. | 564/412 |
| 4,495,368 | 1/1985 | Cordier | 564/412 |
| 4,532,350 | 7/1985 | Cordier et al. | 564/412 |

OTHER PUBLICATIONS

*Chemical Abstracts*, vol. 96, No. 138035d, (1981).
*Chemical Abstracts*, vol. 86, No. 191271x, (1977).

*Primary Examiner*—Bruce Gray
*Attorney, Agent, or Firm*—Craig E. Mixan; Ronald G. Brookens

[57] ABSTRACT

Substituted 2-haloanilines are prepared from the correspondingly substituted 2,4-dichloro- or 2,4-dibromoanilines by selectively reducing a chloro or bromo substituent para to a protected amino group in the presence of the same halogen as an ortho substituent. The selective reductions are accomplished by protecting the amino function of the aniline with two protecting groups, e.g., as the diacetanilide or the succinimide.

9 Claims, No Drawings

PROCESS FOR THE SELECTIVE REDUCTION OF THE 4-HALOGEN IN 2,4-DIHALOANILINES

FIELD OF THE INVENTION

The present invention concerns a process for preparing substituted 2-haloanilines from the correspondingly substituted 2,4-dichloro- or 2,4-dibromoanilines. More particularly, the present invention concerns the selective reduction of a chloro or bromo substituent para to the protected amino group of an aniline also having the same halogen as an ortho substituent.

BACKGROUND OF THE INVENTION

2-Halo and 2,6-dihaloanilines are useful as intermediates in the manufacture of a wide variety of chemical products including, for example, dyes, pharmaceuticals and agricultural chemical. Unfortunately, 2-halo and 2,6-dihaloanilines, optionally substituted in the 3(5)- and/or 6-position, are often not that easy to obtain. Since direct electrophilic halogenation of anilines typically provides little or no selectivity for halogenation at carbons ortho versus para to the amino group, the 4-position must normally be blocked and then deprotected in order to prevent halogenation from occurring there. For example, 2,6-dichloro-3-methylaniline is presently manufactured from the acetanilide of m-toluidine in a multistep process (see O. G. Backeberg et al., *J. Chem. Soc.*, 1943, 78-80; and H. C. Brimelow et al., *J. Chem. Soc.*, 1951 1208-1212) involving the following reaction sequence:

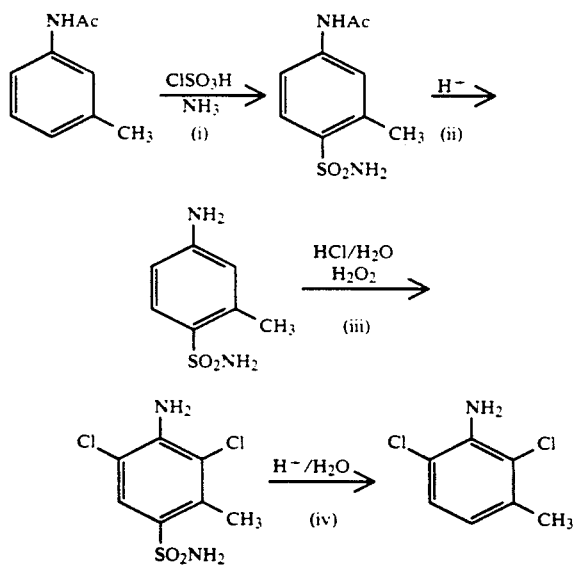

(i) protection of the p-position by sulfonamidation;
(ii) hydrolysis of the acetanilide;
(iii) chlorination of the 2- and 6-positions; and
(iv) deprotection of the p-position The yeilds of the protection (i) and chlorination (iii) steps are relatively low and the use of chlorosulfonic acid and ammonia present difficulties with respect to safe handling and waste disposal.

Rather than employing a scheme which involves the protection and deprotection of the reactive para position, it would be desirable to have a process in which a chloro or bromo substituent in the para position could be selectively removed from readily available anilines also having the same halogen in at least one of the ortho positions.

SUMMARY OF THE INVENTION

The present invention concerns a process for preparing 2-haloanilines of formula (I)

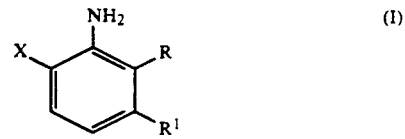

wherein
X is Cl or Br,
R is X, F, $C_1$-$C_4$ alkyl, $C_1$-$C_4$ alkoxy, $CF_3$ or $CO_2R^2$,
$R^1$ is H or $C_1$-$C_4$ alkyl, and
$R^2$ is H or $C_1$-$C_4$ alkyl
which comprises:
(a) contacting an amino-protected 2,4-dichloroaniline or an amino-protected 2,4-dibromoaniline of formula (II)

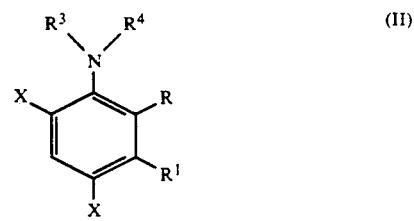

wherein
$R^3$ and $R^4$ are each

where $R^5$ is $CH_3$ or $CH_2CH_3$, or
$R^3$ and $R^4$ taken together are

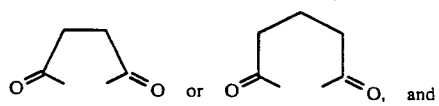

X, R and $R^1$ are as previously defined,
with a hydrogen source in the presence of a palladium catalyst in an inert organic solvent to selectively remove the 4-chloro or 4-bromo substituent; and
(b) hydrolyzing the protecting groups from the amino function to produce the desired aniline.

By protecting the amino function of the aniline with two protecting groups, e.g., as the diacetanilide or the succinimide, a chloro or bromo substituent para to the amino function can be selectively reduced in the presence of the same halogen substituent ortho to the amino function. Thus the present process for preparing 2-haloanilines unsubstituted in the 4-position avoids the need of protecting and deprotecting the position para to the amino group and allows the use of readily available starting materials which have been completely halogenated in all of the available reactive ortho and para positions.

DETAILED DESCRIPTION OF THE INVENTION

As used herein, the term "halo" refers to Cl or Br, and the terms "$C_1$-$C_4$ alkyl" and "$C_1$-$C_4$ alkoxy" refer to straight-chained or branched hydrocarbon groups of up to four carbon atoms, provided that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows: "steric hindrance": A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in "Organic Chemistry" by D. J. Cram and G. Hammond, 2nd edition, McGraw-Hill book Company, N.Y., page 215 (1964).

The preferred "$C_1$-$C_4$ alkyl" and "$C_1$-$C_4$ alkoxy" groups are —$CH_3$, —$CH_2CH_3$, —$OCH_3$ and —$OCH_2CH_3$. The most preferred group is —$CH_3$.

The amino-protected chloroaniline and bromoaniline starting materials of formula II are known compounds, e.g., see Japanese Patent Publication Nos. 52-025117 or 56-164106, or can be prepared from the appropriately substituted chloro- and bromoanilines by conventional acylation procedures. For example, diacetanilides can be prepared from the corresponding chloro- or bromoanilines by treatment with excess acetic anhydride and an acid catalyst, such as, for example, methanesulfonic acid. Alternatively, dipropionamides, succinimides and glutarimides can be prepared from the appropriate chloro- or bromoanilines and the corresponding acid chlorides or bromides, e.g., propionyl, succinyl or glutaryl chloride, in the presence of a hydrogen halide acceptor, such as pyridine or triethylamine. In cases where the aniline contains a bulky ortho substituent, e.g., Br, the introduction of two protecting groups on the amine function may prove difficult and the formation of the diacetanilide {$R^3$ and $R^4$ are each —$C(O)CH_3$} is preferred.

The preferred starting materials are those in which X is Cl or Br, R is Cl, Br, $CH_3$, $OCH_3$ or $CO_2R^2$, $R^1$ is H or $CH_3$, $R^2$ is $CH_3$ or $CH_2CH_3$ and $R^3$ and $R^4$ are —$C(O)CH_3$. The most preferred starting materials are those in which X is Cl, R is Cl or $CO_2R^2$, $R^1$ is H or $CH_3$, $R^2$ is $CH_3$, and $R^3$ and $R^4$ are —$C(O)CH_3$.

The appropriately substituted chloroanilines may in turn conveniently be prepared by protecting the amine moiety of commercially available ortho and meta substituted anilines as the hydrochloride salt, followed by treatment with chlorine. Similarly, appropriately substituted bromoanilines may conveniently be prepared by treatment of commercially available ortho and meta substituted anilines with bromine in acetic acid.

In the reduction step, the amino-protected 2-halo-4-chloro- or bromoaniline is contacted with a hydrogen source in the presence of a palladium catalyst. During the course of the reaction, the halogen in the 4-position is selectively replaced by hydrogen.

The selective reduction is fairly specific to palladium catalysts, and palladium on carbon has generally been found to be more effective than palladium dispersed on other supports. Thus, the preferred catalyst is 1 to 10 percent palladium on carbon. The percent loading of palladium on the carbon support also affects the efficiency of the catalyst depending upon such factors as solvent or hydrogen source. In some instances, 10 percent palladium on carbon functions better than 5 percent or 1 percent palladium on carbon, even though comparisons are based on equal metal content. Generally, 0.01 to 0.20 equivalents of palladium are employed per equivalent of substrate; from 0.02 to 0.10 equivalents are preferred.

The reduction can be conducted using hydrogen gas as the hydrogen source. The hydrogen gas can be continuously sparged into the reaction mixture at atmospheric pressure or the reaction mixture can be pressurized with hydrogen gas in a sealed reactor. With hydrogen gas, however, it is often difficult to control the extent of reduction. This is particularly so when excess hydrogen is sparged into the reaction as is often most convenient. Therefore, it is preferable to use other hydrogen sources.

Formate salts are the most convenient and preferred hydrogen source for the present application. By the term "formate salts" is meant alkali metal formates, such as sodium formate and potassium formate, ammonium formate and trialkylammonium formates wherein the alkyl groups are straight-chained alkyl groups of 1 to 4 carbons, such as triethylammonium formate. The trialkylammonium formates, being relatively non-hygroscopic, easily prepared and quite soluble in most organic solvents, are the preferred hydrogen source.

The trialkylammonium formates can be prepared by stirring an excess of trialkylamine with formic acid in toluene. Removal of the solvent and excess amine by distillation leaves the trialkylammonium formate as a residue which can then be diluted with the desired solvent to give a reagent solution of known concentration. As an alternative to preforming the trialkylammonium formate solution, this reagent can be prepared in situ by the addition of a stoichiometric excess of trialkylamine to 96 percent formic acid in conjunction with the palladium catalyst during the reduction in a fashion similar to that described by Cortese et al., *J. Org. Chem.* 42, 3491 (1977).

The reduction is typically performed using near stoichiometric amounts of reagents. Thus, from 0.9 to 1.1 equivalents of formate salt are employed as the hydrogen source for each equivalent of substrate to be reduced.

However, for more sluggish reactions, for example, those using relatively insoluble alkali metal formates as the hydrogen source, a greater than 10 percent excess of reducing agent can be tolerated without forfeiture of selectivity. If the trialkylammonium formate is prepared in situ, from 0.9 to 1.1 equivalents of formic acid in addition to a 20 to 30 percent stoichiometric excess of trialkylamine are preferred for each equivalent of substrate to be reduced.

The reduction is generally performed in an organic solvent that is inert to the reaction conditions. Aliphatic nitriles and aliphatic alcohols and aromatic hydrocarbons are particularly preferred. With respect to the nitriles, acetonitrile is most preferred. With respect to the alcohols, $C_2$ to $C_4$ alcohols are preferred with secondary and tertiary alcohols being most preferred. 2-Propanol is particularly preferred for those reactions using an alkali metal formate as the hydrogen source.

With respect to aromatic hydrocarbons, toluene is preferred. Aromatic hydrocarbons are acceptable solvents for the trialkylammonium formates but are unacceptable for the alkali metal formates, which are essentially insoluble in this class of solvents.

In general, the reduction is conducted at a temperature between ambient temperature and the reflux temperature of the reaction mixture. Reactions performed using trialkylammonium formate proceed well at room temperature regardless of solvent. With alkali metal formates, on the other hand, operation at reflux is necessary in, for example, acetonitrile. Since higher temperatures can lead to a loss of selectivity and unwanted side-reactions such as dimerization, operation at from room temperature to about 60° C. is preferred.

Operating pressures, although not critical, may also affect the amount of reduction, particularly when using hydrogen gas as the hydrogen source. The pressure may typically vary from atmospheric pressure to about 700 pounds per square inch gauge (psig). Pressures from atmospheric to about 200 psig are preferred.

Since the reduction of the aromatic halogen produces a hydrogen halide and since halides can poison the catalyst, it is often advantageous to add a base to serve as a hydrogen halide acceptor and to buffer the system. At least one equivalent of base should be added for each equivalent of hydrogen halide produced. Suitable bases include the alkali metal acetates, carbonates and bicarbonates: the acetates of sodium and potassium are preferred. The base is preferably added to the substrate prior to the addition of the catalyst.

In a typical reduction, the reducing agent (formate), base and solvent are slurried together with heating. After cooling, the amino-protected 2,4-dihaloaniline is added followed by the palladium on carbon catalyst. The mixture is reacted to completion at which point the catalyst is recovered by filtration and the amino-protected 2-haloaniline is isolated by conventional procedures.

Hydrolysis of the amino-protected 2-haloaniline to the corresponding aniline is conveniently achieved by contacting the protected aniline with water under either basic or acidic conditions. Such hydrolyses are well known to those skilled in the art and are generally conducted in organic solvents that are miscible with water. For example, the protected aniline can be hydrolytically cleaved to the aniline by refluxing in acidic aqueous solution, e.g., 6N HCl in either methanol or acetic acid. The resulting 2-haloaniline can be isolated and purified by routine laboratory procedures, such as azeotropic distillation and fractional distillation or crystal refining.

The following examples are presented to illustrate the invention and should not be construed as limiting the scope of the invention.

All solvents and reagents were obtained from commercial suppliers without further purification, except as noted. Dry acetonitrile was obtained by distillation from $CaH_2$ under an $N_2$ atmosphere. $^1H$ and $^{13}C$ NMR spectra were recorded on a Varian XL-300. Chemical shifts were reported in ppm downfield from an internal tetramethylsilane standard with $CDCl_3$ as the solvent unless otherwise stated. Infrared spectra were obtained on a Perkin-Elmer 683 spectrophotometer as a $CHCl_3$ solution unless otherwise noted. Low resolution electron impact mass spectra were obtained on a Hewlett Packard 5995 GC/MS. Melting points given are uncorrected and the temperature given for Kugelrohr distillations are those of the hot air bath and not necessarily an accurate measure of boiling points.

All compounds are referenced to the structure of Formula II.

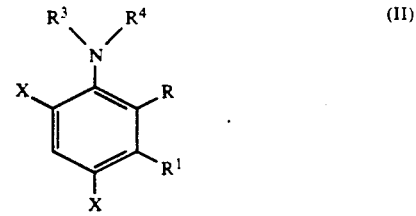

Preparation of Starting Materials (Examples A-K)

General Procedure for Chlorination of Anilines

Dry HCl was bubbled through a solution of commercially available ortho or meta substituted aniline (0.200 mol) in 500 milliliters (mL) of $CCl_4$ and 5 mL of EtOH for 10-15 minutes (min). The salt solution was then cooled in an ice bath and treated with $Cl_2$ gas until the reaction was determined to be complete by gas chromatographic analysis (approximately 10 percent excess $Cl_2$). The reaction mixture was then poured into ice cold MeOH, was taken up in $H_2O$ and extracted three times with $CH_2Cl_2$. The combined organic phases were dried ($Na_2SO_4$), reduced in vacuo and purified by Kugelrohr distillation.

General Procedure for Bromination of Anilines

A commercially available ortho or meta substituted aniline (0.200 mol) in 200 mL of glacial acetic acid, cooled in an ice bath and under $N_2$ atmosphere was treated in a dropwise fashion with bromine (approximately 10 percent excess). The mixture was warmed to ambient temperature and stirred until the reaction was determined to be complete by gas chromatographic analysis. The crude reaction mixture was taken up in $CH_2Cl_2$, washed with water and brine, dried ($Na_2SO_4$), reduced in vacuo and purified by Kugelrohr distillation.

EXAMPLE A

Preparation of Methyl 3,5-Dichloroanthranilate {Formula II: X=Cl, R=$CO_2CH_3$, $R^3$=$R^4$=H}

Dry HCl was bubbled through a solution of methyl anthranilate in $CCl_4$ (420 mL) and ethanol (6 mL) for approximately 30 min, giving a thick, white slurry. The slurry was cooled in an ice bath and chlorine (39.2 g, 553 mmol) was added in several portions over 3 hours (hr). After the reaction was complete (as determined by GC analysis), the reaction mixture was diluted with methanol (100 mL), water (200 mL), and methylene chloride (200 mL). The organic phase was separated, washed with brine (200 mL), and dried over sodium sulfate. The solution was filtered and the solvent was removed by rotoevaporation (maximum bath temperature 45° C.). The crude orange oil (62.9 g) was diluted with cold methanol (300 mL), giving a white solid. The solid was collected by filtration and washed with cold methanol. Drying at 45° C./10 torr gave methyl 3,5-dichloroanthranilate (19.0 g, 39 percent) as a fluffy white solid. mp 63.5°-64.5° C. $^1H$ NMR ($CDCl_3$) δ7.74 (d, J=2.5 Hz, 1H), 7.35 (d, J=2.5 Hz, 1H), 6.23 (br s, 2H), 3.87 (s, 3H); $^{13}C$ NMR ($CDCl_3$) δ167.0, 145.3, 133.2. 129.3, 120.6, 119.7, 112.1, 52.0; MS (70 eV) 219, 187, 159, 124, 97, 62, 28.

EXAMPLE B

Preparation of Methyl 3,5-Dibromoanthranilate {Formula II: X=Br, R=CO$_2$CH$_3$, R$^3$=R$^4$=H}

A solution of methyl anthranilate (28.70 g, 189.9 mmol) in acetic acid (150 mL) was cooled with an ice bath. Bromine (64.83 g, 405.6 mmol) was added slowly dropwise over 50 min. (A considerable amount of insoluble white solid was formed during the bromine addition.) The solution was then removed from the ice bath and stirred at room temperature for 2 hr. The reaction mixture was dissolved in CH$_2$Cl$_2$ (500 mL was required to dissolve the white solid) and the orange solution was washed with a solution of sodium bisulfite giving a pale yellow solution. The organic phase was washed twice with water (250 mL each) and with saturated brine (250 mL). After drying over sodium sulfate, the solvent was removed giving methyl 3,5-dibromoanthranilate (58.10 g, 99 percent) as a pale yellow solid. The product was recrystallized from methanol (300 mL), giving white needles (52.78 g, mp 87.5°-88.5° C.). $^1$H NMR (CDCl$_3$) δ7.95 (d, J=2.1 Hz, 1H), 7.66 (d, J=2.4 Hz, 1H), 6.34 (br s, 2H), 3.88 (s, 3H): $^{13}$C NMR (CDCl$_3$) δ166.9, 146.6, 139.0, 133.0, 112.6, 111.1, 106.5, 52.1: MS (70 eV) 309, 277, 249, 224, 170, 63.

EXAMPLE C

Preparation of 2,4,6-Trichlorodiacetanilide {Formula II: X=Cl, R=Cl, R$^3$=R$^4$=C(O)CH$_3$}

A solution of 2,4,6-trichloroaniline (10.08 g, 51.30 mmol) in acetic anhydride (52.09 g, 510.3 mmol, 48.1 mL) and methanesulfonic acid (0.295 g, 3.07 mmol) was heated at reflux until the reaction was complete. The solution was diluted with CH$_2$Cl$_2$ (50 mL) and washed twice with pH 7.0 phosphate buffer (50 mL each). The organic layer was then washed with brine and dried over sodium sulfate. The solvent and most of the remaining excess acetic anhydride were removed by rotoevaporation. The residual acetic anhydride and other volatiles were removed by Kugelrohr distillation (60° C./4 torr). The product was distilled at 120°-125° C./2.3 torr, giving 2,4,6-trichlorodiacetanilide (13.82 g, 96 percent yield) as a white solid.

The product was recrystallized from either methanol or ethyl acetate/hexane to give white crystals (mp 81°-83° C.). $^1$H NMR (CDCl$_3$) δ7.49 (s, 2H), 2.30 (s, 6H); $^{13}$C NMR (CDCl$_3$) δ171.0, 135.8, 135.6, 134.1, 129 0, 25.6; MS (70 eV) 281, 239, 195, 158, 124, 109, 88, 43.

EXAMPLE D 2,4,6-Tribromodiacetanilide {Formula II: X=Br, R=Br, R$^3$=R$^4$=C(O)CH$_3$}

The title compound was prepared according to the procedure of Example C from 2,4,6-tribromoaniline (16.80 g, 50.94 mmol), acetic anhydride (51.69 g, 506.3 mmol), and methanesulfonic acid (0.324 g, 3.37 mmol). Yield: 20.35 g (97 percent) of white solid by Kugelrohr distillation at 140° C./1.2 torr (mp 96.5°-98.0° C.). $^1$H NMR (CDCl$_3$) δ7.83 (s, 2H), 2.30 (s, 6H); $^{13}$C NMR (CDCl$_3$) δ 170.8, 137.3, 135.3, 125.5, 123.7, 26.0; MS (70 eV) 415, 373, 331, 292, 248, 213, 170, 88, 43.

EXAMPLE E

Methyl 3,5-Dichlorodiacetanthranilate {Formula II: X=Cl, R=CO$_2$CH$_3$, R$^3$=R$^4$=C(O)CH$_3$}

The title compound was prepared according to the procedure of Example C from methyl 3,5-dichloroanthranilate (10.00 g, 45.46 mmol), acetic anhydride (48.62 g, 476.3 mmol), and methanesulfonic acid (0.207 g, 2.15 mmol). Yield: 13.32 g (96 percent) of white solid by Kugelrohr distillation at 130°-135° C./0.9 torr (mp 122°-125° C.). $^1$H NMR (CDCl$_3$)δ7.98 (d, J=2.4 Hz, 1H), 7.74 (d, J=2.4 Hz, 1H), 3.88 (s, 3H), 2.28 (s, 6H); $^{13}$C NMR (CDCl$_3$) δ171.6, 163.4, 135.9, 135.8, 135.4, 133.7, 131.4, 130.3, 52.9, 25.8; MS (70 eV) 305, 261, 226, 219, 187, 160, 124, 88, 43.

EXAMPLE F

Methyl 3,5-Dibromodiacetanthranilate {Formula II: X=Br, R=CO$_2$CH$_3$, R$^3$=R$^4$=C(O)CH$_3$}

The title compound was prepared according to the procedure of Example C from methyl 3,5-dibromoanthranilate (10.00 g, 32.38 mmol), acetic anhydride (34.18 g, 334.8 mmol), and methanesulfonic acid (0.239 g, 2.49 mmol). Yield: 12.04 g (95 percent) of white solid by Kugelrohr distillation at 160°-165° C./3.5 torr (mp 108.5°-112.5° C.). $^1$H NMR (CDCl$_3$) δ8.17 (d, J=2.2 Hz, 1H), 8.05 (d, J=2.4 Hz, 1H), 3.87 (s, 3H), 2.28 (s, 6H); $^{13}$C NMR (CDCl$_3$) δ171.6, 163.3, 139.6, 137.9, 134.0, 131.7, 126.9, 123.2, 53.0, 26.1. MS (70 eV) 393, 351, 309, 277, 240, 170, 143, 88, 43.

EXAMPLE G 2,4,6-Trichloro-3-methyldiacetanilide {Formula II: X=Cl, R=Cl, R$^1$=CH$_3$, R$^3$=R$^4$=C(O)CH$_3$}

2,4,6-Trichloro-3-methylaniline (20 g, 0.114 mol) was heated and stirred at 100° C. for 4-5 hr in acetic anhydride (100 mL) containing a catalytic amount of methanesulfonic acid (1 mL). The excess acetic anhydride and by-product acetic acid was removed on a Buchi evaporator and the product recrystallized from ethyl acetate/hexane to give 26.71 g (80 percent) of product, mp 79°-81° C. IR (Nujol): cm$^{-1}$ (C=0); $^1$H NMR (CDCl$_3$, 60 MHZ) δ2.35 (s, 6, CH$_3$CO), 2.55 (s, 3, CH$_3$), 7.60 (s, 1, aromatic); MS (70 eV), m/z 293 (M$^+$, calcd for C$_{11}$H$_{10}$Cl$_3$NO$_2$: 293).

EXAMPLE H

The following diacetanilides (Table I) were similarly prepared according to the procedures of the preceding examples.

TABLE I

Halodiacetanilides of Formula

| X | R | R$^1$ | % yield | physical property |
|---|---|---|---|---|
| Cl | CF$_3$ | H | 86 | bp 145° C. (2.5 torr) |
| Cl | F | H | 71 | bp 115-130° C. (4.5 torr) |
| Cl | OCH$_3$ | H | 47 | mp 104-106° C. |
| Br | Cl | H | 92 | mp 85-86° C. |
| Br | F | H | 74 | mp 54-57° C. |

TABLE I-continued

Halodiacetanilides of Formula $$\underset{X}{\overset{CH_3(O)C\diagdown N\diagup C(O)CH_3}{\underset{X}{\bigodot}}}\begin{array}{c}R\\R^1\end{array}$$

| X  | R    | R¹ | % yield | physical property |
|----|------|----|---------|-------------------|
| Br | OCH₃ | H  | 87      | mp 96–99° C.      |
| Br | CH₃  | H  | 93      | mp 86–88.5° C.    |

EXAMPLE I 2,4-Dibromo-6-fluorodipropionylanilide {Formula II: $X=Br$, $R=F$, $R^3=R^4=C(O)CH_2CH_3$}

A solution of 9.410 g (35.0 mmol) of 2,4-dibromo-6-fluoroaniline, 18.8 mL (0.216 mol) of propionyl chloride, 15.4 mL (0.110 mol) of triethylamine and 121 mg (0.99 mmol) of dimethylaminopyridine in 100 mL of $CH_2Cl_2$ was heated to reflux for 32 hr. The mixture was cooled, washed with pH 7 phosphate buffered solution (3×30 mL) and brine (30 mL), dried (MgSO₄) and reduced in vacuo. Lower boiling organics were removed by Kugelrohr distillation (80° C., 2 mm). The crude anilide was purified by Kugelrohr distillation (140° C., 2 mm) giving 12.565 g (87 percent) of 2,4-dibromo-6-fluorodipropionylanilide as a white solid (mp 68°–71° C.); ¹H NMR $\delta$1.14 (t, J=7.5 Hz, 6H), 2.59 (q, J=7.5 Hz, 4H), 7.38 (dd, J=8.4, 2.1 Hz, 1H), 7.68 (t, J=2.1 Hz, 1H); ¹³C NMR $\delta$8.6, 31.3, 119.7, 123.5 (d, J=9.3 Hz), 125.9, 126.6 (d, J=15.8 Hz) 131.7 (d, J=23.8 Hz), 158.5 (d, J=240.8 Hz), 174.7.

EXAMPLE J

N-2,4,6-Trichlorophenyl Succinimide {Formula II: $X=Cl$, $R=Cl$, $R^3=R^4=-C(O)CH_2CH_2C(O)-$}

2,4,6-Trichloroaniline (19.6 g 0.1 mol) was dissolved in a 500 mL round bottom flask equipped with a magnetic stirrer and water condenser. Pyridine (19.77 g, 0.25 mol) and succinyl chloride (15.5 g, 0.1 mol) was added and the reaction stirred for 2 hr at room temperature. The reaction was refluxed for an additional 1 hr during which time a considerable amount of black, insoluble material was formed. The solution was poured into water and the product and unreacted aniline isolated by extraction. After drying over MgSO₄ and solvent removal on a Buchi evaporator, the unreacted aniline was removed on a Kugelrohr. The residue was recrystallized from ethyl acetate to give 3.50 g (13 percent) of product (mp 163°–165° C.). IR (Nujol) 16.55 cm⁻¹ (C=O); ¹H NMR (CDCl₃, 60 MHz) $\delta$2.93 (s, 4H, —CH₂CH₂—), 7.54 (s, 2H, aromatic); MS (70 Ev), m/z: 277 ($M^-$, calcd for $C_{10}H_6Cl_3NO_2$: 277).

EXAMPLE K

Preparation of Triethylammonium Formate (Et₃NHHCO₂).

To a solution of triethylamine (33.05 g, 326.7 mmol) in toluene (150 mL) was added 96 percent formic acid (13.81 g, 300.1 mmol) slowly over 5 min. The two-phase system was stirred overnight (17 hr) at ambient temperature. The toluene was removed by distillation (maximum bath temperature 120° C., overhead temperature kept above 100° C.) over several hr. The remaining oil was transferred to a graduated cylinder and the contents sparged with a flow of nitrogen until no noticeable odor of toluene remained. The pale yellow triethylammonium formate (25.35 g, 172.2 mmol, 57.4 percent yield) was diluted to 172.2 mL with acetonitrile giving a 1.0 molar solution. The contents were stored in a serum-capped storage bottle under nitrogen. This or similarly prepared material was used in the following examples whenever preformed triethylammonium formate was called for.

EXAMPLE 1

Reduction of 2,4,6-Trichlorodiacetanilide {Formula II: $X=Cl$, $R=Cl$, $R^3=R^4=C(O)CH_3$}

(a) Sodium formate as hydrogen source 2,4,6-Trichlorodiacetanilide (5.61 g, 0.02 mol) was dissolved in acetonitrile (100 mL). Anhydrous sodium formate (2.72 g, 0.04 mol) was added to the solution along with 2 mol percent Pd/C catalyst (5.60 mg of 5 percent Pd/C). The solution was refluxed under N₂ for 24 hr. Gas chromatographic (GC) analysis indicated 100 percent conversion of starting material and 91 percent (area) of product. The catalyst was filtered from the hot solution; after cooling, the filtrate yielded 0.4 g of insoluble material which was similarly removed by filtration. Evaporation of the filtrate and recrystallization of the residue from ethyl acetate/hexane gave 1.60 g (65 percent) of 2,6-dichlorodiacetanilide {Formula II: $X(2)=Cl$, $X(4)=H$, $R=Cl$, $R^3=R^4=C(O)CH_3$}(mp 59°–62° C.). IR (Nujol): 1725 cm⁻¹ (C=O). The 2,6-dichlorodiacetanilide was hydrolyzed by refluxing in glacial acetic acid containing aqueous HCl for 1 hr. The hydrolyzed product, isolated by removing the solvent and aqueous acid on a Buchi evaporator, had IR, NMR and a MS identical to that of 2,6-dichloroaniline.

(b) Triethylammonium formate (formed in situ) as hydrogen source

Triethylamine (1.025 g, 10.13 mmol) was added to a slurry of sodium acetate (0.822 g, 10.02 mmol) in acetonitrile (20 mL). Formic acid (96 percent, 0.378 g, approx. 8.212 mmol) was added via syringe. The reaction temperature rose from 24° to 29° C. upon adding the formic acid. The solution was heated to reflux (81° C.) for 20 min, and then was cooled to room temperature. 2,4,6-Trichlorodiacetanilide (2.094 g, 7.464 mmol) was added as a solid to the reaction flask, followed by the addition of 10 percent Pd/C (0.378 g, approx. 0.355 mmol Pd). The solution was heated to reflux until the reaction was complete and was then cooled to room temperature. The reaction was allowed to stir for an additional 45 min at room temperature before workup. The reaction mixture was filtered through a Buchner funnel and the residual Pd/C solid rinsed with CH₂Cl₂ (50 mL). The combined organic phases were washed twice with pH 7.0 phosphate buffer (25 mL each) and then with saturated NaCl solution (25 mL). The organic phase was dried over Na₂SO₄, filtered, and the solvent was removed by rotoevaporation (approx. 70° C./10 torr), giving 1.817 g of white, oily solid. The solid was then Kugelrohr distilled. A small amount of oil (0.031 g) was collected at 90° C./1.2 torr, containing a small amount of volatile impurity. The second Kugelrohr fraction (105°–110° C./1.2 torr), a clear oil which solidified upon cooling, was identified as 2,6- dichlorodiacetanilide (1.391 g, 76 percent yield). $^1$H NMR (CDCl$_3$) δ7.50-7.42 (m, 2H), 7.27-7.37 (m, 1H), 2.31 (s, 6H); $^{13}$C NMR (CDCl$_3$) δ171.3, 135.2, 134.9, 130.6, 128.9, 25.7; MS (70 eV) 245, 203, 161, 124, 99, 63, 43.

(c) Hydrogen as hydrogen source 2,4,6-Trichlorodiacetanilide (2.79 g), 50 mL of 2-propanol, 5 mL of pyridine and 106 mg of 10 percent Pd/c were charged into a 200 mL Hastelloy C pressure reactor. The reactor was sealed, purged of air and pressurized to 50 psig with hydrogen. The mixture was stirred overnight at 60° C. at which point the reactor pressure had been reduced to 0 psig. The catalyst was removed by filtration and the filtrate was treated with 2 g of 5N NaOH to hydrolyze the product to a mixture of anilines which had the following composition: 2,4,6-trichloroaniline (49 percent); 2,4-dichloroaniline (1 percent); 2,6-dichloroaniline (43 percent); 2-chloroaniline (2 percent): aniline (1 percent).

A series of reductions of 2,4,6-trichlorodiacetanilide was conducted under a variety of conditions according to the general procedures of Examples 1a and 1b. The product was analyzed by gas chromatography and the results are summarized as relative ratios of volatile components in Table II.

moved on a Buchi evaporator to give 2,6-dichloro-3-methyldiacetanilide {Formula II: X(2)=Cl, X(4)=H, R=Cl, R$^1$=CH$_3$, R$^3$=R$^4$=C(O)CH$_3$} as a viscous oil. IR (Nujol): 1725 cm$^{-1}$ (C=O) $^1$H NMR (CDCl$_3$, 60 MHz), δ2.30 (s, 6H, CH$_3$CO) 2.40 (s, 3H, CH) 7.35 (m, 2H, aromatic). MS (70 eV), m/z 259 (M$^+$, calcd for C$_{11}$H$_{11}$Cl$_2$NO$_2$: 259). Hydrolysis of this product in an aqueous HCl/acetic acid mixture gave, after isolation by extraction, 3.2 g (91 percent) of 2,3-dichloro-3-methylaniline.

EXAMPLE 3

Reduction of Methyl 3,5-Dichlorodiacetanthranilate
{Formula II: X=Cl, R=CO$_2$CH$_3$,
R$^3$=R$^4$=C(O)CH$_3$}

The procedure of Example 1b is repeated using methyl 3,5-dichlorodiacetanthranilate. The product, methyl 3-chlorodiacetanthranilate {Formula II: X(3)=Cl, X(5)=H, R=CO$_2$CH$_3$, R$^3$=R$^4$=C(O)CH$_3$}, was obtained as an oil by Kugelrohr distillation at 130°-135° C./1.4 torr. $^1$H NMR (CDCl$_3$) δ8.00 (dd, J=7.9, 1.5 Hz, 1H), 7.72 (dd, J=8.1, 1.5 Hz, 1H), 7.47 (t, J=8.0 Hz, 1H), 3.87 (s, 3H), 2.28 (s, 6H); $^{13}$C NMR (CDCl$_3$) δ171.9, 164.5, 137.2, 135.0, 134.1, 130.5, 130.2, 129.8, 52.6, 26.0; MS (70 eV) 269, 227, 192, 185, 153, 124, 90, 63, 43.

TABLE II

Reduction of 2,4,6-Trichlorodiacetanilide

| | | | | | | A | B | C | D |
|---|---|---|---|---|---|---|---|---|---|
| H-Source (equiv.) | Equiv. 10% Pd/C | Solvent | Temp °C. | Time (hr) | Additive (equiv.) | % A | % B | % C | % D |
| Et$_3$NHHCO$_2$ (1.0) | 0.05 | CH$_3$CN | RT | 22.5 | NaOAc (1.4) | 0 | 90 | 10 | — |
| Et$_3$NHHCO$_2$ (1.0) | 0.05 | CH$_3$CN | 81 | 1.5 | NaOAc (1.4) | 0 | 85 | 15 | — |
| Et$_3$NHHCO$_2$ (1.0) | 0.02 | CH$_3$CN | 81 | 3.75 | NaOAc (1.4) | 20 | 78 | 1 | — |
| Et$_3$NHHCO$_2$ (0.74) | 0.05 | CH$_3$CN | 81 | 1 | NaOAc (1.4) | 0 | 91 | 9 | — |
| HCO$_2$H (1.09), Et$_3$N (1.42) | 0.05 | CH$_3$CN | RT | 7.5 | — | 4 | 86 | 11 | — |
| HCO$_2$H (1.12), Et$_3$N (1.52) | 0.05 | CH$_3$CN | 81 | 2 | — | 14 | 72 | 13 | — |
| HCO$_2$H (1.15), Et$_3$N (1.46) | 0.05 | CH$_3$CN | RT | 1 | Na$_2$CO$_3$ (1.0) | 19 | 66 | 14 | — |
| HCO$_2$H (1.23), Et$_3$N (1.34) | 0.02 | CH$_3$CN | RT | 20 | — | 15 | 82 | 3 | — |
| HCO$_2$H (1.11), Et$_3$N (1.48) | 0.05 | toluene | 80 | 2.5 | NaOAc (0.2) | 14 | 75 | 11 | — |
| HCO$_2$H (2.00), Et$_3$N (1.00) | 0.05 | CH$_3$CN | 81 | 2 | NaOAc (1.0) | 2 | 85 | 7 | 7 |
| NaHCO$_2$ (1.0) | 0.05 | CH$_3$CN | 81 | 3.5 | NaOAc (1.0) | 18 | 77 | 5 | — |
| NaHCO$_2$ (1.26) | 0.05 | 2-PrOH | 82 | 1.5 | — | 3 | 80 | 16 | 1 |
| NaHCO$_2$ (2.0) | 0.01 | 2-PrOH | 82 | 4.5 | — | 0 | 72 | 28 | — |

EXAMPLE 2

Reduction of 2,4,6-Trichloro-3-methyldiacetanilide
{Formula II: X=Cl, R=Cl, R$^1$=CH$_3$,
R$^3$=R$^4$=C(O)CH$_3$}

2,4,6-Trichloro-3-methyldiacetanilide (5.9 g, 0.02 mol) was dissolved in anhydrous acetonitrile (75 mL) in a 125 mL round bottomed flask and sodium formate (2.72 g 0.04 mol) was added. The reaction mixture was stirred under N$_2$ for 15 min and Pd/C (224 mg, 5 percent Pd/C) was added to reaction mixture. The reaction was followed by GC analysis and the conversion was found to be 55 percent after 24 hr, 83 percent after 48 hr, and 99 percent after 72 hr. The catalyst and inorganics were removed by filtration and the solvent was re-

EXAMPLE 4

Reduction of N-2,4,6-Trichlorophenylsuccinimide
{Formula II: X=Cl, R=Cl,
R$^3$R$^4$=—C(O)CH$_2$CH$_2$C(O)—}

N-2,4,6-Trichlorophenylsuccinimide (1.88 g, 0.05 mol) was dissolved in acetonitrile (25 mL) in a 50 mL round bottomed flask equipped with condenser and magnetic stirrer, and anhydrous ammonium formate (0.63 g, 0.01 mol) was added to the solution. The reaction mixture was stirred for 15 min and Pd/C (188 mg, 5 percent P/C) was added. After 2 hr at reflux, GC analysis showed the conversion was 85 percent with 84 percent selectivity to N-2,6-dichlorophenylsuccinimide {Formula II: X(2)=Cl, X(4)=4, R=Cl, R³R⁴=—C(O)CH₂CH₂C(O)—}. After cooling, the solution was filtered and the solvent removed on a Buchi evaporator. The residue was recrystallized from dichloromethane/hexane to give 0.83 g (50 percent) of product (mp 143°-146° C. IR (Nujol) 1655 cm⁻¹ (C=O). ¹H NMR (CDCl₃, 60 MHz) δ 3.00 (s, 4H, —CH₂CH₂—), 7.47 (m, 3H, aromatic); MS (70 eV), m/z: 243 (M⁻, calcd for C₁₀H₇Cl₂NO₂: 243).

EXAMPLE 5

Reduction of 2,4-dibromo-6-fluorodipropionylanilide {Formula II: X=Br, R=F, R³=R⁴=C(O)CH₂CH₃}

A solution of 2.385 g (6.26 mmol) of 2,4-dibromo-6-fluorodipropionylanilide, 787 mg (12.20 mmol) sodium acetate and 6.2 mL (6.2 mmol) of a 1M triethylammonium formate solution in 33 mL of dry acetonitrile was heated to reflux for 5 min at which time 478 mg of 10 percent Pd/C was added. The mixture was heated to reflux for 27 hr, cooled, filtered and reduced in volume. The crude reaction mixture was taken up in 20 mL of CH₂Cl₂ and was washed with water (3×10 mL) and brine (10 mL). The organic phase was dried (MgSO₄), reduced in vacuo and purified by Kugelrohr distillation (130° C., 2.6 mm) to give 1.202 g (64 percent) of 2-bromo-6-fluorodipropionylanilide {Formula II: X(2)=Br, X(4)=H, R=F, R³=R⁴=C(O)CH₂CH₃} as a colorless oil: ¹H NMR δ 1.14 (t, J=7.3 Hz, 6H), 2.60 (q, J=7.3 Hz, 4H), 7.17 (dt, J=8.1, 1.3 Hz, 1H), 7.30 (dt, J=5.7, 8.1 Hz, 1H), 7.48 (dt, J=1.3, 8.5 Hz, 1H); IR (neat) 2990, 2960, 1723, 1470, 1450, 1350, 1200, 1134, 870, 782 cm⁻¹; mass spectrum (70 eV) 303, (M⁻), 301 (M⁻), 247, 245, 191, 189, 166, 57, 29.

In order to facilitate isolations and purifications, the crude diacetanilides of Examples 6 to 10 were not isolated as such, but rather were converted to the monoacetanilides by partial hydrolysis in mixtures of aqueous caustic and methanol at ambient temperature.

EXAMPLE 6

Reduction of 2,4-Dichloro-6-trifluoromethyldiacetanilide {Formula II: X=Cl, R=CF₃, R³=R⁴=C(O)CH₃}

A solution of 2.00 g (6.37 mmol) of 2,4-dichloro-6-trifluoromethyldiacetanilide, 743 mg (9.06 mmol) of sodium acetate and 6.4 mL (6.4 mmol) of a 1M triethylammonium formate solution in 29 mL of dry acetonitrile was heated to reflux for 5 min at which time 403 mg of 10 percent Pd/C was added. The mixture was heated to reflux for 5.5 hr, cooled, filtered, and reduced in volume. The crude reaction mixture was taken up in 10 mL of MeOH and 10 mL of 10 percent NaOH. After stirring 16 hr at ambient temperature, the solution was poured into 20 mL of H₂O and extracted with CH₂Cl₂ (3×20 mL). The combined organic phases were dried (MgSO₄), reduced in vacuo, purified by Kugelrohr distillation and recrystallization from EtOH to give 914 mg (61 percent) of 2-chloro-6-trifluoromethylacetanilide {Formula II: X(2)=Cl, X(4)=H, R=CF₃, R³=C(O)CH₃} as a white solid (mp 166° C.); ¹H NMR δ 2.23 (s, 3H), 6.98 (br, s, 1H), 7.37 (t, J=7.9 Hz, 1H), 7.60 (d, J=7.9 Hz, 1H), 7.67 (d, J=8.0 Hz, 1H); IR 3420, 1695, 1480, 1450, 1315, 1170, 1133, 1075 cm⁻¹; mass spectrum (70 eV) 237 (M³⁰), 218, 203, 195, 175, 43.

EXAMPLE 7

Reduction of 2,4-Dichloro-6-methoxydiacetanilide {Formula II: X=Cl, R=OCH₃, R³=R⁴=C(O)CH₃}

A solution of 1.368 g (4.96 mmol) of 2,4-dichloro-6-methoxydiacetanilide, 570 mg (6.95 mmol) of sodium acetate and 5.0 mL (5.0 mmol) of a 1M triethylammonium formate solution in 25 mL of dry acetonitrile was heated to reflux for 5 min at which time 276 mg of 10 percent Pd/C was added. The mixture was heated to reflux for 2 hr, cooled, filtered and reduced in volume. The crude reaction mixture was taken up in 10 mL of MeOH and 10 mL of 10 percent NaOH. After stirring 16 hr at ambient temperature, the solution was poured into 20 mL of H₂O and extracted with CH₂Cl₂ (3×20 mL). The combined organic phases were dried (MgSO₄), reduced in vacuo and purified by recrystallization from EtOH to give 704 mg (57 percent) of 2-chloro-6-methoxyacetanilide {Formula II: X(2)=Cl, X(4)=H, R=OCH₃, R³=C(O)CH₃} as a white solid (mp 146.5°-147.5° C.); ¹H NMR δ2.16 (s, 3H), 3.83 (s, 3H), 6.83 (d, J=8.1 Hz, 1H), 6.95 (br s, 1H), 7.03 (d, J=8.1 Hz, 1H), 7.17 (d, J=8.1 Hz, 1H); IR 3420, 1690, 1590, 1490, 1465, 1435, 1270, 1050 cm⁻¹; mass spectrum (70 eV) 201 (M⁺), 199 (M⁺), 164, 157, 142, 43.

EXAMPLE 8

Reduction of 2,4-Dibromo-6-chlorodiacetanilide {Formula II: X=Br, R=Cl, R³=R⁴=C(O)CH₃}

A solution of 1.142 g (3.09 mmol) of 2,4-dibromo-6-chlorodiacetanilide 384 mg (4.68 mmol) of sodium acetate and 3.1 mL (3.1 mmol) of a 1M triethylammonium formate solution in 15 mL of dry acetonitrile was heated to reflux for 5 min at which time 234 mg of 10 percent Pd/C was added. The mixture was heated to reflux for 12 hr, cooled, filtered and reduced in volume. The crude reaction mixture was taken up in 10 mL of MeOH and 10 mL of 10 percent NaOH. After stirring 16 hr at ambient temperature, the solution was poured into 20 mL of H₂O and extracted with CH₂Cl₂ (3×20 mL). The combined organic phases were dried (MgSO₄), reduced in vacuo and purified by Kugelrohr distillation to give 381 mg (49 percent) of 2-bromo-6-chloroacetanilide {Formula II: X(2)=Br, X(4)=H, R=Cl, R³=C(O)CH₃} as a white solid (mp 186°-189° C.); ¹H NMR δ 2.24 (s, 3H), 6.99 (br s, 1H), 7.10 (dd, J=8.1, 7.4 Hz, 1H), 7.41 (d, J=8.1 Hz, 1H), 7.54 (d, J=7.4 Hz, 1H); IR 3420, 1695, 1485, 1450, 1430, 1370 cm⁻¹; mass spectrum (70 eV) 249 (M⁺), 247 (M⁺), 207, 205, 168, 43.

EXAMPLE 9

Reduction of 2,4-Dibromo-6-methoxydiacetanilide {Formula II: X=Br, R=OCH₃, R³=R⁴=C(O)CH₃}

A solution of 1.850 g (5.07 mmol) of 2,4-dibromo-6-methoxydiacetanilide, 805 mg (7.60 mmol) of sodium carbonate and 5.1 mL (5.1 mmol) of a 1M triethylammonium formate solution in 25 mL of dry acetonitrile was heated to reflux for 5 min at which time 372 mg of 10 percent Pd/C was added. The mixture was heated to reflux for 5.5 hr, cooled, filtered and reduced in volume. The crude reaction mixture was taken up in 10 mL of MeOH and 10 mL of 10 percent NaOH. After stirring 16 hr at ambient temperature, the solution was poured into 20 mL of H₂O and extracted with CH₂Cl₂ (3×20 mL). The combined organic phases were dried ($MgSO_4$), reduced in vacuo and purified by recrystallization from EtOH to give 243 mg (20 percent) of 2-bromo-6-methoxyacetanilide {Formula II: X(2)=Br, X(4)=H, R=$OCH_3$, $R^3$=$C(O)CH_3$} as a white solid (mp 158° C.); $^1$H NMR δ 2.19 (br s, 3H), 3.84 (s, 3H), 6.78 (br s, 1H), 6.89 (d, J=8.1 Hz, 1H), 7.13 (t, J=8.1 Hz, 1H), 7.25 (d, J=8.1 Hz, 1H); IR 3415, 1680, 1585, 1571, 1485, 1460, 1428, 1262, 1037 cm$^{-1}$; mass spectrum (70 eV) 245 (M$^+$), 243 (M$^+$), 203, 201, 188, 186, 164, 169, 158, 43.

EXAMPLE 10

Reduction of 2,4-Dibromo-6-methyldiacetanilide {Formula II: X=Br, R=$CH_3$, $R^3$=$R^4$=$C(O)CH_3$}

A solution of 550 mg (1.58 mmol) of 2,4-dibromo-6-methyldiacetanilide, 200 mg (2.43 mmol) of sodium acetate and 1.6 mL (1.6 mmol) of a 1M triethylammonium formate solution in 10 mL of dry acetonitrile was heated to reflux for 5 min at which time 104 mg of 10 percent Pd/C was added. The mixture was heated to reflux for 6.5 hr, cooled, filtered and reduced in volume. The crude reaction mixture was taken up in 10 mL of MeOH and 10 mL of 10 percent NaOH. After stirring 16 hr at ambient temperature, the solution was poured into 20 mL of $H_2O$ and extracted with $CH_2Cl_2$ (3×20 mL). The combined organic phases were dried ($MgSO_4$), reduced in vacuo and purified by recrystallization from EtOH to give 204 mg (57 percent) of 2-bromo-6-methylacetanilide {Formula II: X(2)=Br, X(4)=H, R=$CH_3$, $R^3$=$C(O)CH_3$} as a white solid (mp 164°-166° C.); $^1$H NMR (D$_6$-DMSO) δ 2.03 (s, 3H), 2.17 (s, 3H), 7.10 (t, J=7.5 Hz, 1H), 7.25 (d, J=7.5 Hz, 1H), 7.47 (d, J=7.5 Hz, 1H), 9.50 (br s, 1H); IR 3415, 1690, 1480, 1370, 1245 cm$^{-1}$; mass spectrum (70 eV) 229 (M$^+$), 227 (M$^+$), 187, 185, 148, 106, 43.

What is claimed is:

1. A process for preparing 2-haloanilines of formula (I)

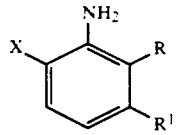

wherein
X is Cl or Br,
R is X, F, $C_1$-$C_4$ alkyl, $C_1$-$C_4$ alkoxy, $CF_3$ or $CO_2R^2$,
$R^1$ is H or $C_1$-$C_4$ alkyl, and
$R^2$ is H or $C_1$-$C_4$ alkyl
which comprises:
(a) contacting an amino-protected 2,4-dichloroaniline or an amino-protected 2,4-dibromoaniline of formula (II)

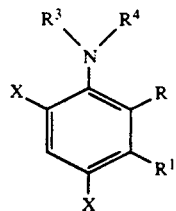

wherein
$R^3$ and $R^4$ are each

where $R^5$ is $CH_3$ or $CH_2CH_3$, or
$R^3$ and $R^4$ taken together are

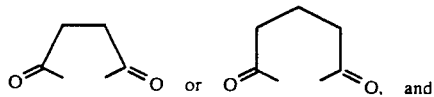

X, R and $R^1$ are as previously defined,
with a hydrogen source in the presence of a palladium catalyst in an inert organic solvent to selectively remove the 4-chloro or 4-bromo substituent; and
(b) hydrolyzing the protecting groups from the amino function to produce the desired aniline.

2. The process of claim 1 in which X is Cl or Br, R is Cl, Br, $CH_3$, $OCH_3$, $CF_3$ or $CO_2R^2$, $R^1$ is H or $CH_3$, $R^2$ is $CH_3$ or $CH_2CH_3$, and $R^3$ and $R^4$ are —$C(O)CH_3$.

3. The process of claim 2 in which X is Cl, R is Cl or $CO_2R^2$, $R^1$ is H or $CH_3$, $R^2$ is $CH_3$, and $R^3$ and $R^4$ are —$C(O)CH_3$.

4. The process of claim 1 in which the palladium catalyst is 1 to 10 percent palladium on carbon.

5. The process of claim 1 in which the hydrogen source is an alkali metal formate, ammonium formate, or a trialkylammonium formate wherein the alkyl groups are straight-chained alkyl groups of 1 to 4 carbons.

6. The process of claim 1 in which the hydrogen source is hydrogen gas.

7. The process of claim 1 in which the inert organic solvent is an aliphatic nitrile, an aliphatic alcohol or an aromatic hydrocarbon.

8. The process of claim 1 in which the reduction is conducted at a temperature between ambient temperature and the reflux temperature of the reaction mixture.

9. The process of claim 1 which is optionally conducted in the presence of a base.

* * * * *